United States Patent
Hendrikse et al.

(10) Patent No.: US 10,345,264 B2
(45) Date of Patent: Jul. 9, 2019

(54) DOPANTS FOR THE DETECTION OF NITRATES

(71) Applicant: Smiths Detection Montreal Inc., Mississauga (CA)

(72) Inventors: Jan Hendrikse, Whitby (CA); Vladimir Romanov, Vaughan (CA); Udo Verkerk, Toronto (CA); Alan Hopkinson, Toronto (CA)

(73) Assignee: SMITHS DETECTION MONTREAL INC., Mississauga (CA)

( * ) Notice: Subject to any disclaimer, the term of this patent is extended or adjusted under 35 U.S.C. 154(b) by 0 days.

(21) Appl. No.: 15/569,822

(22) PCT Filed: Apr. 28, 2016

(86) PCT No.: PCT/IB2016/052408
§ 371 (c)(1),
(2) Date: Oct. 27, 2017

(87) PCT Pub. No.: WO2016/174605
PCT Pub. Date: Nov. 3, 2016

(65) Prior Publication Data
US 2018/0136165 A1    May 17, 2018

(30) Foreign Application Priority Data

Apr. 28, 2015  (GB) .................................. 1507246.5

(51) Int. Cl.
*H01J 49/00*    (2006.01)
*G01N 27/64*   (2006.01)
(Continued)

(52) U.S. Cl.
CPC .............. *G01N 27/64* (2013.01); *B01J 45/00* (2013.01); *G01N 27/62* (2013.01); *G01N 27/68* (2013.01); *H01J 49/145* (2013.01); *G01N 27/622* (2013.01)

(58) Field of Classification Search
CPC ........ H01J 49/00; H01J 49/0027; H01J 49/02; H01J 49/0422; H01J 49/26; G01N 27/00; G01N 27/62; G01N 27/64
(Continued)

(56) References Cited

U.S. PATENT DOCUMENTS

| | | | |
|---|---|---|---|
| 2005/0061964 A1* | 3/2005 | Nagano | H01J 49/0027 250/281 |
| 2015/0004710 A1 | 1/2015 | Gregory et al. | |
| 2016/0282321 A1* | 9/2016 | Syage | H01J 49/10 |

FOREIGN PATENT DOCUMENTS

| | | |
|---|---|---|
| CA | 2918705 A1 | 1/2015 |
| CA | 2904479 A1 | 3/2016 |
| WO | 2014058508 A2 | 4/2014 |

OTHER PUBLICATIONS

Cotte-Rodriguez, Desorption Electrospray Ionization of Explosives on Surfaces: Sensitivity and Selectivity Enhancement by Reactive Desorption Electrospray Ionization, 2005, Anal. Chem, 77, pp. 6755-6764. (Year: 2005).*

(Continued)

*Primary Examiner* — Jason L McCormack
(74) *Attorney, Agent, or Firm* — Kevin E. West; Advent, LLP

(57) ABSTRACT

The present disclosure relates to an ion exchange process, as well as a process and system for detecting nitrates, which employ a class of dopants comprising at least two functional groups capable of simultaneous convergent hydrogen bonding with a nitrate ion. In an aspect, the present disclosure (Continued)

Figure 1:
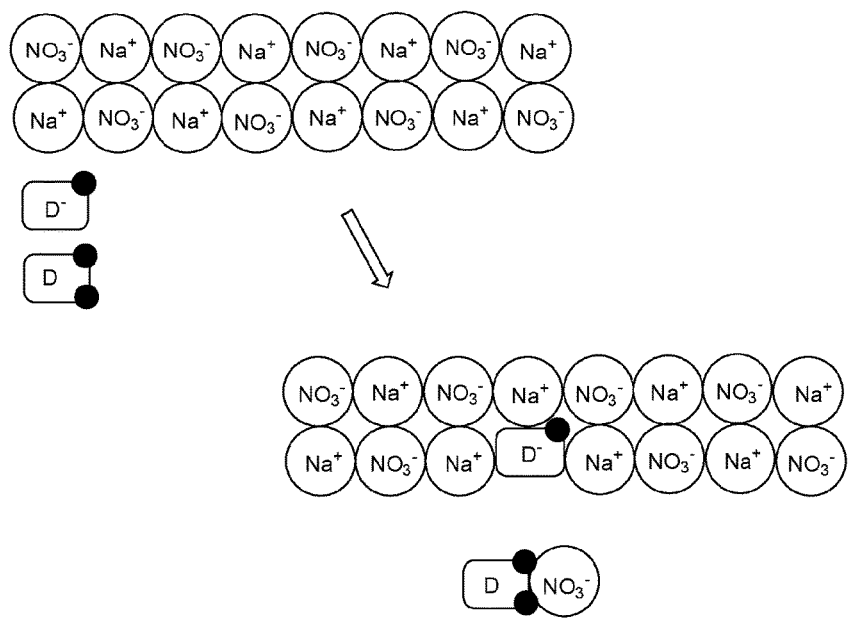

provides an ion exchange process for forming a negatively charged nitrate-dopant ion analyte for analysis by a spectrometry analysis instrument, comprising: providing a gas comprising a dopant in both neutral and ionized forms; contacting a nitrate-containing sample with the gas comprising the dopant and thereby desorbing a nitrate ion from the sample to form a negatively charged nitrate-dopant ion analyte and replacing the desorbed nitrate ion with a negatively charged ionized dopant molecule; wherein the dopant is an organic compound comprising two or more carbon atoms and two or more functional groups capable of simultaneous convergent hydrogen bonding with a nitrate ion; or the dopant is an organic compound comprising at least two carbon atoms and only a single functional group capable of hydrogen bonding with a nitrate ion, which group is a —COOH functional group, and where the carbon atom of the —COOH functional group is bonded directly to another carbonyl group; and with the proviso that the dopant is not lactic acid, a lactic acid salt or a compound that forms lactate ions upon ionization.

20 Claims, 2 Drawing Sheets

(51) Int. Cl.
  *G01N 27/62* (2006.01)
  *H01J 49/14* (2006.01)
  *G01N 27/68* (2006.01)
  *B01J 45/00* (2006.01)

(58) Field of Classification Search
  USPC .......................................... 250/281, 282, 288
  See application file for complete search history.

(56) References Cited

OTHER PUBLICATIONS

International Search Report dated Jul. 22, 2016 for PCT/US2016/052408.
Creaser, Colin et al., "Ion mobility spectrometry: a review. Part 1. Structural analysis of mobility measurement", The Analyst, 129: 984-994, Published 2004, p. 986, col. 1.
Puton, J. et al., "Ion mobility spectrometers with doped gases", Talanta, vol. 76, pp. 978-987, Published 2008.
Waraksa, E. et al., "Dopants and gas modifiers in ion mobility spectroscopy", Trends in Analytical Chemistry, vol. 82, pp. 237-249, Published 2016.
Search Report for Patent Appl No. GB1507246.5, dated Jul. 22, 2016.
Combined Search and Examination Report for Patent Appln No. GB1607375.1, dated Feb. 21, 2017.
Extended Search Report for European Patent Appln No. 16786045.1, dated Oct. 26, 2018.
Cotte-Rodriguez, et al., "Desorption Electrospray Ionization of Explosives on Surfaces: Sensitivity and Selectivity Enchancement by Reactive Desorption Electrospray Ionization," Analytical Chemistry, vol. 77, No. 21, Nov. 1, 2005, pp. 6755-6764.
Gapeev, et al., "Liquid chromatography/mass spectrometric analysis of explosives: RDX adduct ions," Rapid Communications in Mass Spectrometry, Feb. 2003, pp. 943-948.

\* cited by examiner

DOPANTS FOR THE DETECTION OF NITRATES

The present disclosure relates to an ion exchange process, as well as a process and system for detecting nitrates, which employ a class of dopants comprising at least two functional groups capable of simultaneous convergent hydrogen bonding with a nitrate ion. This class of dopants is capable of desorbing a nitrate ion from a sample as part of an ion exchange to form a nitrate-dopant analyte ion which may be detected by a spectrometry analysis instrument.

In one aspect of the disclosure, there is provided an ion exchange process for forming a negatively charged nitrate-dopant ion analyte for analysis by a spectrometry analysis instrument. The process comprises: providing a gas comprising a dopant in both neutral and ionized forms; contacting a nitrate-containing sample with the gas comprising the dopant and thereby desorbing a nitrate ion from the sample to form a negatively charged nitrate-dopant ion analyte and replacing the desorbed nitrate ion with a negatively charged ionized dopant molecule.

In another aspect of the disclosure, there is provided a process for detecting a nitrate ion in a sample. The process comprises: providing a gas comprising a dopant in both neutral and ionized forms; conducting ion exchange with the sample by contacting the sample with the gas comprising the dopant; and detecting ions produced as a result of ion exchange using a spectrometry analysis instrument. In embodiments, the sample is a nitrate-containing sample and ion exchange involves desorbing a nitrate ion from the sample to form a negatively charged nitrate-dopant ion analyte and replacing the desorbed nitrate ion with a negatively charged ionized dopant molecule.

In a further aspect of the disclosure, there is provided a nitrate ion detection system. The system comprises: a dopant; an ionization source; and a spectrometry analysis instrument. The ionization source is configured for receiving and emitting a gas comprising the dopant and for generating ionized dopant within the ionization source to form a gas comprising a dopant in both its neutral and ionized forms. The ionization source is further configured for directing the gas comprising dopant out of the ionization source so as to contact a nitrate-containing sample arranged on a surface and located proximal to the ionization source and thereby desorbing a nitrate ion from the sample to form a negatively charged nitrate-dopant ion analyte and replacing the desorbed nitrate ion with a negatively charged ionized dopant molecule. The spectrometry analysis instrument is configured for receiving and analyzing the nitrate-dopant ion analyte.

In yet a further aspect of the disclosure, there is provided a use of a gas comprising a dopant, in both its neutral and ionized forms, for detecting a nitrate ion in a sample by ion exchange.

In the above aspects of the present disclosure, the dopant employed is an organic compound comprising two or more carbon atoms and two or more functional groups capable of simultaneous convergent hydrogen bonding with a nitrate ion; with the proviso that the dopant is not lactic acid, a lactic acid salt or a compound that forms lactate ions upon ionization. Alternatively, the dopant compound described in the above aspects may be substituted by an organic compound comprising at least two carbon atoms and only a single functional group capable of hydrogen bonding with a nitrate ion, which group is a —COOH functional group, and where the carbon atom of the —COOH functional group is bonded directly to another carbonyl group. In exemplary embodiments, the dopant is glyoxylic acid.

Figure 2:
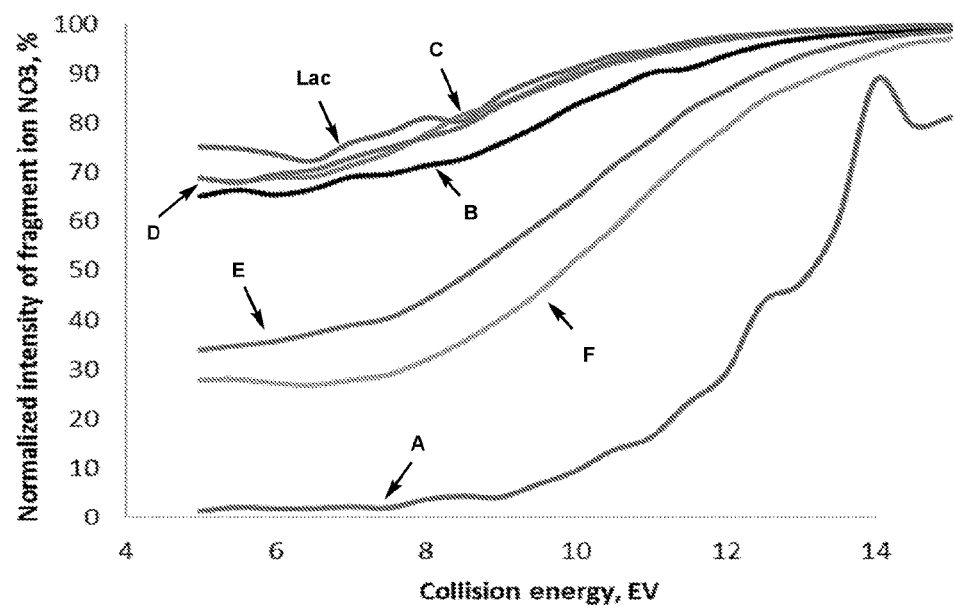
Figure 3:
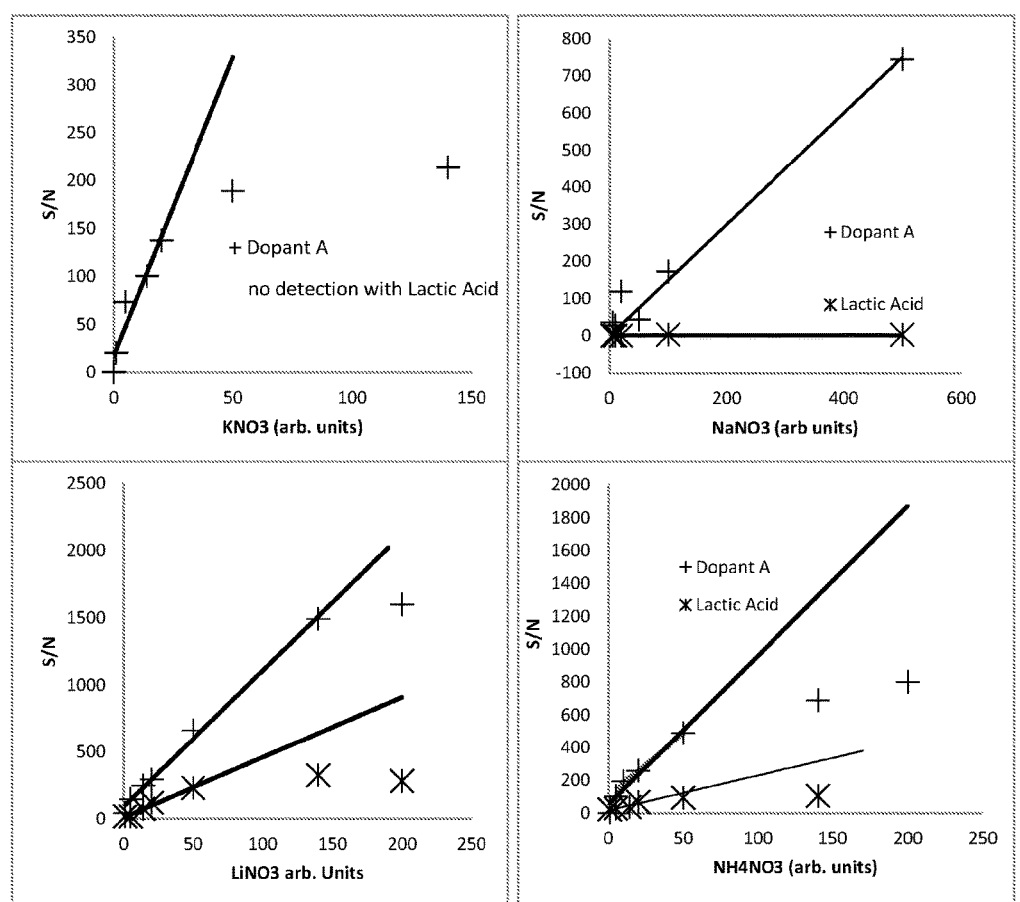

Embodiments of the disclosure will now be described, by way of example only, with reference to the accompanying Figures, in which:

FIG. 1 corresponds to an ion exchange reaction scheme involving desorption of a nitrate ion from a sample, formation of nitrate-dopant analyte ion, and replacement of the desorbed nitrate ion of the sample with a negatively charged dopant molecule;

FIG. 2 corresponds to collision energy scans of nitrate-dopant analyte ion complexes showing the intensity of fragment ions as a function of collision energy in a triple quad MS instrument for six different dopants—oxalic acid (A), fumaric acid (B), glyoxylic acid (C), glycolic acid (D), succinic acid (E) and malonic acid (F)—according to the present disclosure, in comparison with lactic acid ("Lac"); and FIG. 3 shows a comparison of sensitivity measurements for nitrate ions in nitrate salts of $NH_4$, Li, Na and K as a function of dopant where a gas flow in an Low Temperature Plasma (LTP) surface ionization is doped with dopant A (oxalic acid) or lactic acid dopant.

The dopant compound comprises two or more functional groups capable of simultaneous convergent hydrogen bonding with a nitrate ion. In particular, each functional group comprises a proton which is capable of forming, together with a proton of another of the two or more functional groups, simultaneous convergent hydrogen bonds with a nitrate ion.

In embodiments, the calculated Gibbs free energy of binding of the nitrate-dopant ion analyte formed in the processes of the present disclosure is greater than for a nitrate-lactate ion, as measured using theoretical computer modeling at the B3LYP/6-21+G(d) level of theory (for example, with Gaussian, Games, Q-chem, or Molpro software packages).

FIG. 2 corresponds to different collision energy scans for nitrate-dopant analyte ions formed in accordance with the present disclosure in comparison with nitrate-lactate ions and shows the relationship between intensity of the fragment ions as a function of collision energy, as determined experimentally. The collision energy scans allow for an evaluation of the binding energies of the nitrate-dopant analyte ions. The results demonstrate that the binding energies of the nitrate-dopant analyte ions formed in accordance with the process of the present disclosure, namely where oxalic acid, fumaric acid, glyoxylic acid, glycolic acid, succinic acid and malonic acid dopants are employed, are superior to the binding energy of nitrate-lactate analyte ions.

In embodiments, two or more functional groups of the dopant which are capable of simultaneous convergent hydrogen bonding with a nitrate ion are selected from —COOH, —OH, —$NH_2$ and —$NHR_w$, wherein $R_w$ is an electron-withdrawing group. In some embodiments, $R_w$ is selected from —C(O)—R, —C(O)—OR, —$CF_3$, —$SO_2$—R, or an optionally substituted aryl group, wherein R is a substituted or unsubstituted hydrocarbyl group, for example a $C_1$-$C_6$ linear or branched alkyl group. The aryl group may be a $C_6$ to $C_{10}$ aromatic group which may optionally have 1 to 3 substitutents selected from —C(O)—R, —C(O)—OR, —$CF_3$ and —$SO_2$—R, where R is defined as above.

Where reference is made to the number of carbon atoms above, this is the total number of carbon atoms of the dopant compound including any carbon atoms of the functional groups capable of simultaneous convergent hydrogen bonding with a nitrate ion.

In embodiments, the dopant is a $C_2$ or $C_{4+}$ organic compound comprising at least two functional groups capable of simultaneous convergent hydrogen bonding with a nitrate ion selected from —COOH, —OH, —$NH_2$ and —$NHR_w$, wherein $R_w$ is an electron-withdrawing group; or the dopant is a $C_3$ organic compound comprising at least two functional groups capable of simultaneous convergent hydrogen bonding with a nitrate ion selected from —COOH, —OH, —$NH_2$ and —$NHR_w$, wherein $R_w$ is an electron-withdrawing group, provided that a single —COOH functional group is not present in combination with a single —OH group.

For the avoidance of doubt, where $C_n$ or $C_{n+}$ are referred to herein, this denotes the total number of carbon atoms of the dopant compound including any carbon atoms of the functional groups capable of simultaneous convergent hydrogen bonding with a nitrate ion. $C_{n+}$ indicates that n or more total carbon atoms are present.

In embodiments, the dopant is a $C_2$ or $C_4$ organic compound comprising at least two functional groups capable of simultaneous convergent hydrogen bonding with a nitrate ion selected from —COOH, —OH, —$NH_2$ and —$NHR_w$, wherein $R_w$ is an electron-withdrawing group. In some embodiments, the functional groups may be selected from —COOH, —OH and —$NH_2$. In other embodiments, the functional groups may be selected from —COOH and —OH. The two or more functional groups capable of simultaneous convergent hydrogen bonding with a nitrate ion may be the same or different. In exemplary embodiments, the functional groups are different and the dopant is glycolic acid.

In embodiments, the dopant is a $C_{2+}$ organic compound comprising at least two —COOH functional groups capable of simultaneous convergent hydrogen bonding with a nitrate ion and optionally additional functional groups capable of simultaneous convergent hydrogen bonding with a nitrate ion selected from —OH, —$NH_2$ and —$NHR_w$, wherein $R_w$ is an electron-withdrawing group. In some embodiments, the dopant is a $C_2$-$C_6$ organic compound. In other embodiments, the dopant compound is a $C_2$-$C_4$ organic compound. In exemplary embodiments, the dopant is selected from oxalic acid, malonic acid, succinic acid and fumaric acid. In other exemplary embodiments, the dopant is oxalic acid.

Ionization of a gas comprising the dopant forms a mixture of the dopant in both its neutral and ionized forms, which may lead to the formation of a dimer, D-D⁻, of the neutral and ionized forms. Thus, in some embodiments, the neutral and ionized forms of the dopant form a dimer, D-D⁻, in the gas phase.

Without being bound by any particular theory, it is believed that the dimer formed may take part in an ion exchange reaction with a nitrate ion of a sample, as illustrated by the reaction scheme according to FIG. 1. As part of the ion exchange, a nitrate ion is desorbed from the sample and forms a hydrogen bonded adduct with the neutral dopant molecule of the dimer leading to the production of a nitrate-dopant analyte ion. The protons of the dopant compound are therefore not donated in order to form a nitrate-dopant analyte ion, as for instance would be expected in acid-base reaction. Meanwhile, the desorbed nitrate ion of the sample is replaced by the negatively charged ionized dopant molecule of the dimer. Alternatively, the neutral and ionized forms of the dopant may interact with the sample to give rise to ion exchange without necessarily forming a dimer. In either case, it is possible that no net change in charge is observed in the sample as a result of replacement of the nitrate ion with the negatively charge dopant molecule.

In embodiments, the sample employed in the processes of the disclosure may be arranged on a surface and/or the process may involve surface ionization of the sample. In embodiments, the sample is a non-volatile liquid or a non-volatile solid. In some embodiments, the ion exchange reaction occurs at the interface between the solid/liquid sample and the gas phase comprising the dopant.

In embodiments, the sample is of biological origin. In further embodiments, the sample is an industrial work piece or pharmaceutical product or ingredient. In further embodiments, the sample is a food or food ingredient, a toxin, a drug, an explosive, a bacterium, or a biological tissue.

In embodiments, the sample is located in an ambient environment and/or is not heated during the process.

In some embodiments, the sample comprises or consists essentially of an organic nitrate salt. For example, the organic nitrate salt may be urea nitrate. In other embodiments, the sample comprises or consists essentially of an inorganic nitrate salt. For example, the inorganic nitrate salt is selected from ammonium nitrate, lithium nitrate, sodium nitrate, potassium nitrate, or a combination thereof.

In embodiments, providing a gas comprising a dopant in both neutral and ionized forms comprises providing an ionization source configured to receive and emit a flow of gas comprising the dopant. In embodiments, this step of the process may further comprise applying a voltage between first and second electrodes of the ionization source to generate an electric field. In embodiments, this step of the process may additionally comprise introducing a gas doped with the dopant into the ionization source to form a gas comprising the dopant in both neutral and ionized forms. In embodiments, this step of the process may additionally comprise directing the gas comprising dopant in both neutral and ionized forms which is emitted from the ionization source to the sample which is arranged on a surface proximal to the ionization source.

The gas employed herein which may comprise the dopant and flow through the ionization source may be any suitable gas of which the skilled person is familiar. In embodiments, the gas comprises air, compressed air or dried air. However, it is contemplated that a variety of other gases, such as nitrogen, argon or helium, may be used as the carrier gas.

In embodiments, the ionization source is an atmospheric pressure chemical ionization (APCI) source, a dielectric barrier discharge (DBD) ionization source, a Corona discharge ionization source, a glow discharge ionization source, an ionization source which implements alpha radiation from Americium-241 (Am241) or a desorption electrospray ionization (DESI) source.

Further details of suitable ionization sources for providing the gas comprising the dopant in both its neutral and ionized forms and for contacting a sample arranged on a surface proximal thereto are provided in WO 2014/117271. Such ionization sources may be used in combination with an on-demand vapour generator, as described in WO 2014/045067.

Ionization sources which generate significant amounts of nitrates have hitherto not been considered particularly suitable for the detection of nitrate ions in a sample due to the high amount of nitrates detected in the background. In the processes of the present disclosure a nitrate-dopant ion analyte is formed as described hereinbefore. Without being bound by any particular theory, the class of dopants used in accordance with the present disclosure are efficient in binding a nitrate ion and producing the nitrate-dopant ion analyte which may be detected as a result of having two or more functional groups capability of simultaneous convergent hydrogen bonding with a nitrate ion. This increases the sensitivity of the detection in the spectrometry analysis instrument, making such ionization sources more suitable for the detection of nitrate ions in a sample.

FIG. 3 shows sensitivity measurements for nitrate ions in nitrate salts of $NH_4$, Li, Na and K as a function of dopant, where a gas flow in an LTP surface ionization is doped with dopant A (oxalic acid) in accordance with the process of the disclosure in comparison with lactic acid dopant not in accordance with the present disclosure. Use of dopant A (oxalic acid) improves the limit of detection of nitrate ions by approximately a factor of 20 on average across the different salts tested and is shown to be far superior than lactic acid.

In an exemplary embodiment, the ionization source is a Low Temperature Plasma (LTP) probe. The LTP probe generates significant amounts of nitrates. Using an LTP probe as the ionization source has many advantages, not least the low temperature requirements, and ambient conditions in which the sample may be located.

In an alternative embodiment, the ionization source is a $Ni^{63}$ based ionization source, which generates very little nitrate ions.

In embodiments, the spectrometry analysis instrument is an ion mobility spectrometer, a mass spectrometer or a combination thereof.

The spectrometry analysis instrument may employ any of a number of mass spectrometry techniques including Ion Trap, Quadruple, Time of Flight, Magnetic Sector, Orbitrap, combinations thereof, and so forth, for mass-selection of ions, and/or ion mobility spectrometry techniques such as Ion Mobility Spectrometry (IMS), Field Asymmetric Ion Mobility Spectrometry (FAJMS), Traveling Wave Ion Mobility Spectrometry (TWTMS), Standing Wave IMS, combinations thereof, and so forth for mobility-selection of ions. The ions may be detected by a detector of the spectrometry analysis instrument appropriate for the selection (separation) technique(s) used.

In embodiments, the spectrometry analysis is connected to a capillary interface through which the analyte ions may be directed. For example, the capillary interface may include a capillary connected to a capillary casing. The capillary interface may be configured for heating the ionized analytes received from the sample (i.e. a heated capillary interface).

Embodiments of the present disclosure described hereinbefore may be combined with any other compatible embodiments to form further embodiments of the disclosure.

The invention claimed is:

1. An ion exchange process for forming an analyte for analysis by a spectrometry analysis instrument, comprising:
   providing a gas comprising a dopant in both neutral and ionized forms;
   contacting a nitrate-containing sample with the gas comprising the dopant and thereby desorbing a nitrate ion from the sample to form a negatively charged nitrate-dopant ion analyte and replacing the desorbed nitrate ion with a negatively charged ionized dopant molecule;
   wherein the dopant comprises at least one of an organic compound comprising two or more carbon atoms and two or more functional groups capable of simultaneous convergent hydrogen bonding with a nitrate ion; or an organic compound comprising at least two carbon atoms and only a single functional group capable of hydrogen bonding with a nitrate ion, which group is a —COOH functional group, and where the carbon atom of the —COOH functional group is bonded directly to another carbonyl group; and
   wherein the dopant is not lactic acid, a lactic acid salt or a compound that forms lactate ions upon ionization.

2. A process for detecting a nitrate ion in a sample, comprising:
   providing a gas comprising a dopant in both neutral and ionized forms;
   conducting ion exchange with the sample by contacting the sample with the gas comprising the dopant; and
   detecting ions produced as a result of the ion exchange using a spectrometry analysis instrument;
   wherein the dopant comprises at least one of an organic compound comprising two or more carbon atoms and two or more functional groups capable of simultaneous convergent hydrogen bonding with a nitrate ion; or an organic compound comprising at least two carbon atoms and only a single functional group capable of hydrogen bonding with a nitrate ion, which group is a —COOH functional group, and where the carbon atom of the —COOH functional group is bonded directly to another carbonyl group; and
   wherein the dopant is not lactic acid, a lactic acid salt or a compound that forms lactate ions upon ionization.

3. A process according to claim 2, wherein the sample is a nitrate-containing sample, and conducting ion exchange involves desorbing a nitrate ion from the sample to form a negatively charged nitrate-dopant ion analyte and replacing the desorbed nitrate ion with a negatively charged ionized dopant molecule.

4. A process according to claim 1, wherein the sample is arranged on a surface, and the process involves further comprises surface ionization of the sample.

5. A process according to claim 1, wherein the neutral and ionized forms of the dopant form a dimer, D-D⁻, in the gas phase.

6. A process according to claim 1, wherein the dopant comprises two or more functional groups capable of simultaneous convergent hydrogen bonding with a nitrate ion, the two or more functional groups being selected from —COOH, —OH, —$NH_2$, and —$NHR_w$, wherein $R_w$ is an electron withdrawing group selected from —C(O)—R, —C(O)—OR, —$CF_3$, —SO2-R, or an aryl group, and wherein R is a substituted hydrocarbyl group or an unsubstituted hydrocarbyl group.

7. A process according to claim 1, wherein the dopant is a $C_3$ organic compound comprising at least two functional groups capable of simultaneous convergent hydrogen bonding with a nitrate ion, the two or more functional groups being selected from —COOH, —OH, —$NH_2$ and —$NHR_w$, wherein $R_w$ is an electron-withdrawing group, and wherein a single —COOH functional group is not present in combination with a single —OH group.

8. A process according to claim 1, wherein the dopant is a $C_2$ or $C_{4+}$ organic compound comprising at least two functional groups capable of simultaneous convergent hydrogen bonding with a nitrate ion, the at least two functional groups being selected from —COOH, —OH, —$NH_2$ and —$NHR_w$, wherein $R_w$ is an electron-withdrawing group.

9. A process according to claim 1, wherein the dopant is a $C_2$ or $C_4$ organic compound.

10. A process according to claim 8, wherein the at least two functional groups of the dopant are different.

11. A process according to claim 10, wherein the dopant is glycolic acid or glyoxylic acid.

12. A process according to claim 6, wherein the dopant is a $C_{2+}$ organic compound comprising at least two —COOH functional groups capable of simultaneous convergent hydrogen bonding with a nitrate ion.

13. A process according to claim 12, wherein the dopant is selected from oxalic acid, malonic acid, succinic acid and fumaric acid.

14. A process according to claim 1, wherein the sample comprises an organic nitrate salt or an inorganic nitrate salt.

15. A process according to claim 14, wherein the organic nitrate salt is urea nitrate.

16. A process according to claim 14, wherein the inorganic nitrate salt is selected from ammonium nitrate, lithium nitrate, sodium nitrate, potassium nitrate, or a combination thereof.

17. A process according to claim 1, wherein providing a gas comprising a dopant in both neutral and ionized forms includes providing an ionization source configured to receive and emit a flow of gas, the flow of comprising the dopant.

18. A process according to claim 17, wherein the ionization source comprises a Low Temperature Plasma probe or a $Ni^{63}$ based ionization source.

19. A process according to claim 1, wherein the spectrometry analysis instrument comprises an ion mobility spectrometer, a mass spectrometer or a combination thereof.

20. A nitrate ion detection system, comprising:
a dopant;
an ionization source, the ionization source configured for receiving and emitting a gas comprising the dopant and for generating ionized dopant within the ionization source to form a gas comprising a dopant in both its neutral and ionized forms, the ionization source further configured for directing the gas comprising a dopant in both its neutral and ionized forms out of the ionization source so as to contact a nitrate-containing sample arranged on a surface and located proximal to the ionization source and thereby desorbing a nitrate ion from the sample to form a negatively charged nitrate-dopant ion analyte and replacing the desorbed nitrate ion with a negatively charged ionized dopant molecule; and
a spectrometry analysis instrument configured for receiving and analyzing the nitrate-dopant ion analyte;
wherein the dopant comprises at least one of an organic compound including two or more carbon atoms and two or more functional groups capable of simultaneous convergent hydrogen bonding with a nitrate ion; or an organic compound including at least two carbon atoms and only a single functional group capable of hydrogen bonding with a nitrate ion, which group is a —COOH functional group, and where the carbon atom of the —COOH functional group is bonded directly to another carbonyl group; and
wherein the dopant is not lactic acid, a lactic acid salt or a compound that forms lactate ions upon ionization.

\* \* \* \* \*